United States Patent
Owen et al.

(10) Patent No.: US 9,714,908 B2
(45) Date of Patent: Jul. 25, 2017

(54) SUB-PIXEL ANALYSIS AND DISPLAY OF FINE GRAINED MINERAL SAMPLES

(71) Applicant: FEI Company, Hillsboro, OR (US)

(72) Inventors: Michael James Owen, Geebung (AU); Garth Howell, McDowall (AU); Ashley Donaldson, Gordon Park (AU)

(73) Assignee: FEI Company, Hillsboro, OR (US)

( * ) Notice: Subject to any disclaimer, the term of this patent is extended or adjusted under 35 U.S.C. 154(b) by 267 days.

(21) Appl. No.: 14/073,523

(22) Filed: Nov. 6, 2013

(65) Prior Publication Data

US 2015/0122992 A1 May 7, 2015

(51) Int. Cl.
 *G21K 7/00* (2006.01)
 *G01N 23/225* (2006.01)

(52) U.S. Cl.
 CPC ..... *G01N 23/225* (2013.01); *G01N 2223/402* (2013.01); *G01N 2223/616* (2013.01); *H01J 2237/225* (2013.01); *H01J 2237/2442* (2013.01)

(58) Field of Classification Search
 USPC .... 250/306, 307, 310, 311; 378/5, 8–12, 29, 378/46, 49, 53, 82, 83, 87, 90, 98.6, 98.9, 378/113, 121, 145, 146, 210; 702/40, 46, 702/49, 75, 76, 78, 134, 172; 252/1, 252/408.1, 965
 See application file for complete search history.

(56) References Cited

U.S. PATENT DOCUMENTS

| | | | |
|---|---|---|---|
| 4,037,101 | A | 7/1977 | Okumura et al. |
| 4,476,386 | A | 10/1984 | Reid et al. |
| 4,592,082 | A | 5/1986 | Pawloski |
| 4,807,148 | A | 2/1989 | Lacey |
| 4,839,516 | A | 6/1989 | Freeman et al. |

(Continued)

FOREIGN PATENT DOCUMENTS

| | | |
|---|---|---|
| CN | 100498309 C | 6/2009 |
| JP | 2000249668 A | 9/2000 |

(Continued)

OTHER PUBLICATIONS

Christopher Hess, Larg H. Weiland; Proc. IEEE 1998 Int. Conference on Microelectronic Test Structures, vol. 11, Mar. 1998,"Wafer Level Defect Density Distribution Using Checkerboard Test Structures".*

(Continued)

*Primary Examiner* — Bernard Souw
(74) *Attorney, Agent, or Firm* — Scheinberg & Associates, P.C.; John E. Hillert; Michael O. Scheinberg

(57) ABSTRACT

Method and apparatus for analysis and display of fine grained mineral samples. A portion of the sample is illuminated with a charged particle beam. Emitted radiation is detected, and a sample emission spectrum is generated and fit with a plurality of standard emission spectra of minerals in a candidate mineral composition. A mineral composition whose emission spectrum best fits the sample emission spectrum is selected from a plurality of candidate mineral compositions. An assigned color is received for each mineral in the selected mineral composition, and the assigned colors are blended according to the proportion of each mineral in the selected mineral composition. An image pixel corresponding to the portion of the sample is rendered for display.

18 Claims, 9 Drawing Sheets

(56) References Cited

U.S. PATENT DOCUMENTS

| | | | |
|---|---|---|---|
| 5,555,198 | A | 9/1996 | Asano |
| 5,597,538 | A * | 1/1997 | Taylor et al. .................. 423/3 |
| 5,741,707 | A | 4/1998 | Herron et al. |
| 5,798,525 | A | 8/1998 | Benizri-Carl et al. |
| 5,866,903 | A | 2/1999 | Morita et al. |
| 5,906,919 | A | 5/1999 | Garini et al. |
| 5,991,028 | A | 11/1999 | Cabib et al. |
| 6,018,587 | A | 1/2000 | Cabib |
| 6,066,459 | A | 5/2000 | Garini et al. |
| 6,072,178 | A * | 6/2000 | Mizuno .................. 250/310 |
| 6,122,343 | A | 9/2000 | Pidcock |
| 6,282,301 | B1 | 8/2001 | Haskett |
| 6,341,257 | B1 | 1/2002 | Haaland |
| 6,377,652 | B1 | 4/2002 | Sturm |
| 6,385,281 | B1 | 5/2002 | Ozawa et al. |
| 6,407,386 | B1 * | 6/2002 | Dotan et al. ................ 250/310 |
| 6,452,177 | B1 * | 9/2002 | Feldman et al. ................ 850/9 |
| 6,466,929 | B1 | 10/2002 | Brown et al. |
| 6,470,335 | B1 | 10/2002 | Marusak |
| 6,584,413 | B1 * | 6/2003 | Keenan et al. ................ 702/28 |
| 6,658,143 | B2 | 12/2003 | Hansen et al. |
| 6,674,894 | B1 | 1/2004 | Parker et al. |
| 6,675,106 | B1 * | 1/2004 | Keenan et al. ................ 702/28 |
| 6,687,620 | B1 | 2/2004 | Haaland et al. |
| 6,724,940 | B1 | 4/2004 | Qian et al. |
| 6,842,702 | B2 | 1/2005 | Haaland et al. |
| 6,993,170 | B2 | 1/2006 | Johnson et al. |
| 7,139,415 | B2 | 11/2006 | Finkbeiner |
| 7,202,475 | B1 * | 4/2007 | Testoni .................. 250/310 |
| 7,243,030 | B2 | 7/2007 | Reeve et al. |
| 7,400,770 | B2 | 7/2008 | Keaton et al. |
| 7,790,465 | B2 | 9/2010 | Otvos |
| 8,664,595 | B2 * | 3/2014 | Buhot et al. ................ 250/306 |
| 8,828,279 | B1 * | 9/2014 | Zamkov et al. ......... 252/519.4 |
| 8,880,356 | B2 * | 11/2014 | Corbett ............. G01N 23/2076 250/307 |
| 9,188,555 | B2 * | 11/2015 | Owen ................ G01N 23/2252 |
| 2002/0169589 | A1 | 11/2002 | Banki et al. |
| 2004/0027350 | A1 | 2/2004 | Kincaid et al. |
| 2004/0147830 | A1 | 7/2004 | Parker et al. |
| 2005/0037515 | A1 | 2/2005 | Nicholson et al. |
| 2006/0028643 | A1 | 2/2006 | Gottlieb et al. |
| 2008/0192987 | A1 | 8/2008 | Helgason et al. |
| 2011/0044426 | A1 | 2/2011 | Ullberg et al. |
| 2011/0144922 | A1 * | 6/2011 | Corbett et al. ................ 702/28 |
| 2011/0155907 | A1 | 6/2011 | Bushell |
| 2014/0001356 | A1 * | 1/2014 | Buhot et al. ................ 250/307 |
| 2014/0032131 | A1 * | 1/2014 | Owen ............................ 702/28 |
| 2014/0117229 | A1 | 5/2014 | Owen |
| 2014/0117231 | A1 | 5/2014 | Owen et al. |
| 2014/0117234 | A1 | 5/2014 | Owen |

FOREIGN PATENT DOCUMENTS

| | | |
|---|---|---|
| JP | 2001066269 A | 3/2001 |
| RU | 2054660 C1 | 2/1996 |
| WO | WO9905503 A2 | 2/1999 |

OTHER PUBLICATIONS

Goergen E.,"From SEM & EDS Maps to Numbers in Unconventional Reservoirs", Characterizing Oil & Gas Reservoirs Webcast Series, FEI Company, accessed Nov. 6, 2013.

Unknown, http://en.wikipedia.org/wiki/Oil_reserves, accessed Aug. 15, 2013.

Sutherland, D.N. et al., "Application of Automated Quantitative Mineralogy in Mineral Processing," Minerals Engineering, 1991, pp. 753-762, vol. 4, Nos. 7-11.

Gottlieb, P. et al., "The Automatic Identification and Quantification of Silver Minerals," XVIII International Mineral Processing Congress, May 23-28, 1993, pp. 475-481, Sydney, Australia.

Sutherland, David N., "Image Analysis for Off-Line Characterisation of Mineral Particles and Prediction of Processing Properties," Part. Part. Syst. Charact., 1993, pp. 271-274, vol. 10.

Meyer, K., et al., 'Qualitative and Quantitative Mixture Analysis by Library Search: Infrared Analysis of Mixtures of Carbohydrates,' Analytica Chimica Acta, Sep. 1, 1993, pp. 161-171, vol. 281.

Creelman, Robert A. et al., "A Scanning Electron Microscope Method for Automated, Quantitative Analysis of Mineral Matter in Coal," International Journal of Coal Geology, 1996, pp. 249-269, vol. 30.

Newbury, Dale E., "Chemical Compositional Mapping by Microbeam Analysis at the Micrometer Scale and Finer," Microelectronics Journal, 1997. pp. 489-508, vol. 28.

Ghassemian, Hassan et al., "Object-Oriented Feature Extraction Method for Image Data Compaction," IEEE Control Systems Magazine, Jun. 1998, pp. 42-48.

Ashton, Edward A. et al., "Multialgorithm Solution for Automated Multispectral Target Detection," Opt. Eng., Apr. 1999, pp. 717-724, vol. 38, No. 4.

Gottlieb, P. et al., "Using Quantitative Electron Microscopy for Process Mineralogy Applications," Microtextural Mineralogy, Apr. 2000, pp. 24-25.

Tellinghuisen, Joel, 'On the Role of Statistical Weighting in the Least-Squares Analysis of UV-Visible Spectrophotometric Data,' Applied Spectroscopy, 2000, pp. 1208-1213, vol. 54, No. 8.

Hazel, Geoffrey G., "Object-level Processing of Spectral Imagery for Detection of Targets and Changes Using Spatial-Spectral-Temporal Techniques," Proceeding of the SPIE, 2001, pp. 380-390, vol. 4381.

Benz, Ursula C. et al., "Multi-resolution, Object-oriented Fuzzy Analysis of Remote Sensing Data for GIS-ready Information," ISPRS Journal of Photogrammetry & Remote Sensing, 2004, pp. 239-258, vol. 58.

Kern, Denise, I. et al., 'Two sub-states of the red2 state of methyl-coenzyme M reductase revealed by high-field EPR spectroscopy,' J. Biol. Inorg. Chem., Aug. 10, 2007, pp. 1097-1105, vol. 12.

* cited by examiner

SUB-PIXEL ANALYSIS AND DISPLAY OF FINE GRAINED MINERAL SAMPLES

TECHNICAL FIELD OF THE INVENTION

The present invention relates to analysis and display of the mineral content of samples containing fine grained minerals.

BACKGROUND OF THE INVENTION

Scanning electron microscopy-energy dispersive X-ray spectroscopy (SEM-EDS) systems are used to obtain and analyze x-ray emission spectra from mineral samples in order to determine sample composition. A mineral sample is raster scanned via an electron beam, and x-ray emission spectra are recorded on a per pixel basis and analyzed to assign a single mineral to each pixel. Two currently existing methods used to identify and assign a mineral are outlined here. In the first, the sample x-ray emission spectrum is compared to single mineral x-ray emission spectra stored in a library, and a mineral with the closest matching x-ray emission spectrum is assigned to the pixel. In the second, the sample x-ray emission spectrum is fit to a linear combination of elemental x-ray emission spectra stored in a library. A least squares algorithm is used to determine the percentage of each element in the combination and how well the spectrum of the linear combination fits the sample spectrum. The elemental percentages are then used to identify the closest matching mineral (e.g., one having the same elements and percentages) from a catalogue of mineral definitions, and that mineral is assigned to the pixel. Other methods include integrating energy regions to obtain a photon count associated with an element; and matching a collection of integrated photon counts against a catalogue of mineral definitions. The energy ranges may be as narrow as 1 channel, or as wide as the peak of an EDS signal.

The methods described above adequately identify sample composition on a per pixel basis when the grain size of minerals in the sample is larger than the pixel size of the raster scan. If the grain size of minerals in the sample is smaller than the pixel size, the pixel size can be reduced by increasing the resolution of the SEM. However, a natural limit is reached when the pixel size becomes smaller than the x-ray interaction volume or the volume within which x-rays are produced in the sample at a given SEM resolution. At this limit, the measured signal originates in a physical volume in the material that cannot be reduced by further reducing the pixel size or increasing the SEM resolution. For conventional beam energies of 15 keV-20 keV the volume is on the order of 1 µm-3 µm, and this occurs in certain common and economically important mineral samples, such as shales, marls and laterites.

In fine grained mineral samples, two or more minerals can contribute to the recorded x-ray emission spectrum because the mineral grains are smaller than the x-ray interaction volume. Although this volume is a direct function of the accelerating voltage of the electron beam, it cannot be reduced because doing so would require generating an electron beam having insufficient energy to excite x-ray emissions of the elements in the sample. This beam voltage requirement therefore limits the minimum usable beam voltage to a range of approximately 10 kV-20 kV. At these beam energies, the clay mineral grains in a shale sample are often much smaller than the x-ray interaction volume. As a result, the closest matching single mineral spectra returned by either of the previously described known mineral analysis techniques can be inaccurate or incomplete.

The least squares method used to fit a combination of elemental spectra to the sample spectrum has also been used to fit a combination of mineral spectra to the sample spectrum. While this technique, in principle, could allow for sub-pixel mineral identification in samples that are non-homogeneous at the scanned pixel level, it is difficult to resolve the contributions of different minerals to the overall sample spectrum since many mineral spectra have overlapping peaks. This makes it extremely difficult to determine the relative proportion of the elemental x-ray signals that are due to different minerals within the pixel

SUMMARY OF THE INVENTION

An object of the invention is to provide a computer implemented method for displaying a mineral composition of a sample. A portion of the sample is illuminated with a charged particle beam. A sample emission spectrum is generated from detected emissions from the sample. The sample emission spectrum is fit with a plurality of candidate emission spectra, each candidate emission spectrum including a combination of emission spectra from a plurality of minerals in proportions that are determined by the fit to the sample emission spectrum. An emission spectrum is identified from among the plurality of candidate emission spectra based on a quality of fit to the sample emission spectrum. The identified emission spectrum comprises a plurality of identified minerals in a respective plurality of identified proportions. A plurality of colors respectively corresponding to the plurality of identified minerals is received, and an image pixel corresponding to the illuminated portion of the sample is rendered by blending the plurality of colors respectively corresponding to the plurality of identified minerals according to the respective plurality of identified proportions. The charged particle beam can be an electron beam, a proton beam or an ion beam. The sample emission spectrum can be an x-ray emission spectrum from detected x-ray emissions from the sample. The sample emission spectrum can be fit with the plurality of candidate emission spectra using a least squares analysis.

An additional aspect of some embodiments of the invention provides a computer implemented method for displaying a mineral composition of a sample. A portion of the sample is illuminated with a charged particle beam. A sample emission spectrum is generated from detected emissions from the sample. A plurality of candidate mineral compositions is received from a list of candidate mineral compositions. Each candidate mineral composition includes a plurality of minerals. For each of the plurality of candidate mineral compositions, a proportion for each of the plurality of minerals in the candidate mineral composition is determined by fitting the sample emission spectrum with a candidate emission spectrum formed from a combination of emission spectra from the plurality of minerals in the candidate mineral composition. A candidate mineral composition whose candidate emission spectrum is a best fit to the sample emission spectrum is identified. A plurality of colors respectively corresponding to the plurality of minerals in the identified candidate mineral composition is received. An image pixel corresponding to the illuminated portion of the sample is rendered by blending the plurality of colors respectively corresponding to the plurality of minerals in the identified candidate mineral composition according to the determined proportion for each of the plurality of minerals. The charged particle beam can be an electron beam, a proton beam or an ion beam. The sample emission spectrum can be an x-ray emission spectrum generated from detected x-ray emissions from the sample.

An additional aspect of some embodiments of the invention provides an apparatus for determining and displaying the mineral composition of a sample. A charged particle beam source illuminates a portion of the sample. A detector detects radiation emitted from the illuminated portion of the sample. One or more computer processors execute instructions stored on a machine readable medium in order to perform one or more of the following functions. Generate a sample emission spectrum from the detected radiation emitted from the illuminated portion of the sample. Fit the sample emission spectrum with a plurality of candidate emission spectra, where each candidate emission spectrum including a combination of the emission spectra from a plurality of minerals in proportions that are determined by the fit to the sample emission spectrum. Identify an emission spectrum from among the plurality of candidate emission spectra based on a quality of fit to the sample emission spectrum, where the identified emission spectrum comprises a plurality of identified minerals in a respective plurality of identified proportions. Receive a plurality of colors respectively corresponding to the plurality of identified minerals. And render an image pixel corresponding to the illuminated portion of the sample by blending the plurality of colors respectively corresponding to the plurality of identified minerals according to the respective plurality of identified proportions. The charged particle beam source can be at least one of an electron beam source, a proton beam source or an ion beam source. The sample emission spectrum can be an x-ray emission spectrum generated from detected x-ray emissions from the sample. The sample emission spectrum can be fit with a plurality of candidate emission spectra using a least squares analysis.

Another aspect of some embodiments of the invention provides an apparatus for determining and displaying the mineral composition of a sample. A charged particle beam source illuminates a portion of the sample. A detector detects radiation emitted from the illuminated portion of the sample. One or more computer processors execute instructions stored on a machine readable medium in order to perform one or more of the following functions. Generate a sample emission spectrum from the detected radiation emitted from the illuminated portion of the sample. Receive a plurality of candidate mineral compositions from a list of candidate mineral compositions, where each candidate mineral composition includes a plurality of minerals. Determine, for each of the plurality of candidate mineral compositions, a proportion for each of the plurality of minerals in the candidate mineral composition by fitting the sample emission spectrum with a candidate emission spectrum formed from a combination of emission spectra from the plurality of minerals in the candidate mineral composition. Identify a candidate mineral composition whose candidate emission spectrum is a best fit to the sample emission spectrum. Receive a plurality of colors respectively corresponding to the plurality of minerals in the identified candidate mineral composition. And render an image pixel corresponding to the illuminated portion of the sample by blending the plurality of colors respectively corresponding to the plurality of minerals in the identified candidate mineral composition according to the determined proportion for each of the plurality of minerals. The charged particle beam source can be an electron beam source, a proton beam source or an ion beam source. The sample emission spectrum can be an x-ray emission spectrum from detected x-ray emissions from the sample.

An additional aspect of some embodiments of the invention provides a non-transitory computer readable medium that includes instructions for causing a programmable processor to perform one or more of the following functions. Generate a sample emission spectrum from radiation emitted from a portion of the sample illuminated with a charged particle beam. Fit the sample emission spectrum with a plurality of candidate emission spectra, wherein each candidate emission spectrum comprises a combination of the emission spectra from a plurality of minerals in proportions that are determined by the fit to the sample emission spectrum. Identify an emission spectrum from among the plurality of candidate emission spectra based on a quality of fit to the sample emission spectrum, wherein the identified emission spectrum comprises a plurality of identified minerals in a respective plurality of identified proportions. Receive a plurality of colors respectively corresponding to the plurality of identified minerals. And render an image pixel corresponding to the illuminated portion of the sample by blending the plurality of colors respectively corresponding to the plurality of identified minerals according to the respective plurality of identified proportions. The instructions to fit the sample emission spectrum with a plurality of candidate emission spectra can include instructions to fit the sample emission spectrum using a least squares analysis.

An additional aspect of some embodiments of the invention provides a non-transitory computer readable medium that includes instructions for causing a programmable processor to perform one or more of the following functions. Generate a sample emission spectrum from the radiation emitted from a portion of the sample illuminated with a charged particle beam. Receive a plurality of candidate mineral compositions from a list of candidate mineral compositions, wherein each candidate mineral composition includes a plurality of minerals. Determine, for each of the plurality of candidate mineral compositions, a proportion for each of the plurality of minerals in the candidate mineral composition by fitting the sample emission spectrum with a candidate emission spectrum formed from a combination of emission spectra from the plurality of minerals in the candidate mineral composition. Identify a candidate mineral composition whose candidate emission spectrum is a best fit to the sample emission spectrum. Receive a plurality of colors respectively corresponding to the plurality of minerals in the identified candidate mineral composition. And render an image pixel corresponding to the illuminated portion of the sample by blending the plurality of colors respectively corresponding to the plurality of minerals in the identified candidate mineral composition according to the determined proportion for each of the plurality of minerals.

The foregoing has outlined rather broadly the features and technical advantages of the present invention in order that the detailed description of the invention that follows may be better understood. Additional features and advantages of the invention will be described hereinafter. It should be appreciated by those skilled in the art that the conception and specific embodiments disclosed may be readily utilized as a basis for modifying or designing other structures for carrying out the same purposes of the present invention. It should also be realized by those skilled in the art that such equivalent constructions do not depart from the spirit and scope of the invention as set forth in the appended claims.

BRIEF DESCRIPTION OF THE DRAWINGS

For a more thorough understanding of the present invention, and advantages thereof, reference is now made to the following descriptions taken in conjunction with the accompanying drawings, in which.

DETAILED DESCRIPTION OF PREFERRED EMBODIMENTS

Although much of the previous description is directed at mineral samples from drill cores, the invention could be used to prepare samples of any suitable material. The terms "work piece," "sample," "substrate," and "specimen" are used interchangeably in this application unless otherwise indicated. Further, whenever the terms "automatic," "automated," or similar terms are used herein, those terms will be understood to include manual initiation of the automatic or automated process or step.

In the following discussion and in the claims, the terms "including" and "comprising" are used in an open-ended fashion, and thus should be interpreted to mean "including, but not limited to . . . ." To the extent that any term is not specially defined in this specification, the intent is that the term be given its plain and ordinary meaning. The accompanying drawings are intended to aid in understanding the present invention and, unless otherwise indicated, are not drawn to scale. Particle beam systems suitable for carrying out the present invention are commercially available, for example, from FEI Company, the assignee of the present application.

Figure 1:
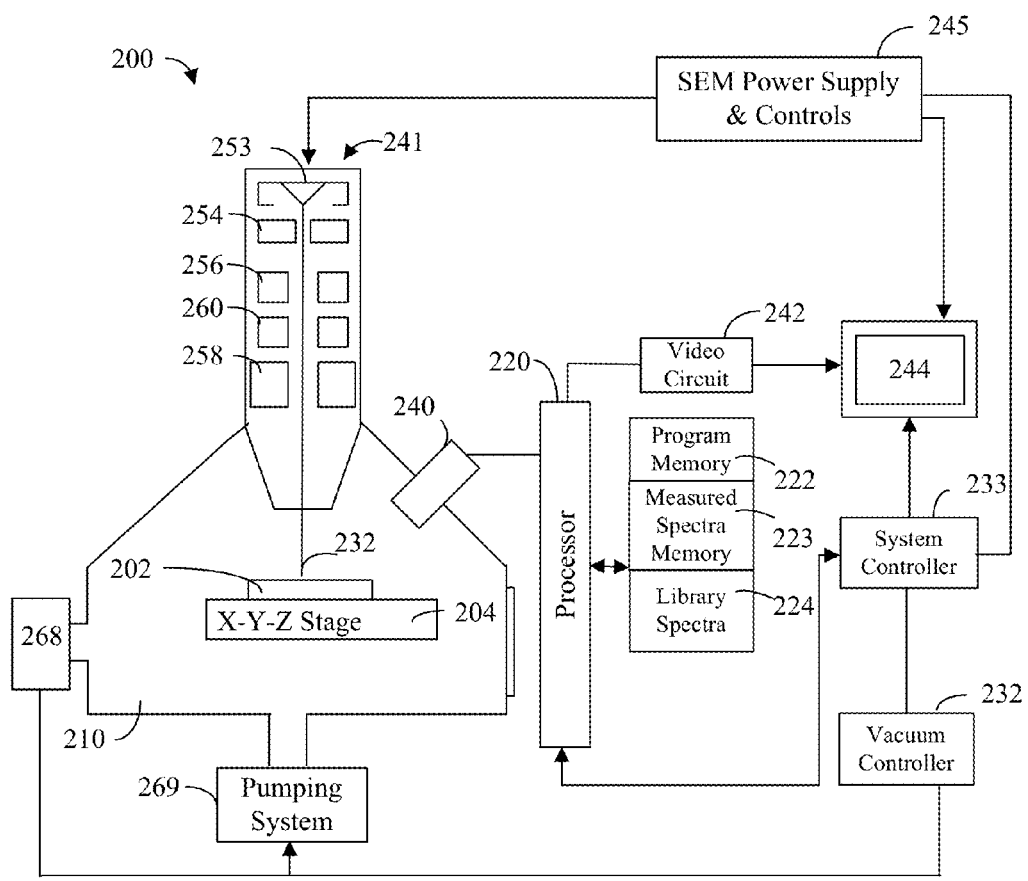
FIG. 1 is an illustration of a mineral identification system 200 used to raster scan a mineral sample and perform mineral identification on a per pixel basis.

FIG. 1 is an illustration of a mineral identification system 200 used to raster scan a mineral sample and perform mineral identification on a per pixel basis. The mineral identification system 200 includes a scanning electron beam system 241 and an x-ray detector 240. An electron beam 232 emitted from a cathode 253 is accelerated toward an anode 254. Electron beam 232 is subsequently focused to a fine spot by means of a condensing lens 256 and an objective lens 258, and can be deflected across a sample 202 by means of a deflection coil 260 to perform a two-dimensional raster scan of the sample. The condensing lens 256, objective lens 258, and deflection coil 260 are supplied current by a power supply 245 operated under the control of a system controller 233. The sample 202 is preferably mounted on a movable X-Y stage 204 within a lower vacuum chamber 210. The vacuum chamber 210 is evacuated to high vacuum by a mechanical pumping system 269 and an ion pump 268 operated under the control of vacuum controller 232.

When the electron beam 232 strikes the sample 202, x-rays that are characteristic of the elements in the sample 202 are emitted. The emitted x-rays are detected by x-ray detector 240, which preferably outputs a signal indicative of the energy of the detected x-rays. To that end, x-ray detector 240 is preferably an energy dispersive detector such as a silicon drift detector. However, other types of x-ray detectors can be employed. The output signal of x-ray detector 240 can be amplified, and the amplified signal recorded by processor 220. Processor 220 can be programmed to store, for each scanned pixel, a histogram counting the total number of detected x-rays in each of a plurality of energy bins over some range of energy. Typically, the energy range is on the order of 0-10 keV, and is subdivided into energy bins of 10-20 eV, for a total of 500 to 1000 energy bins or channels per pixel.

System 200 also includes a display 244 for displaying the results of the mineral analysis and other information by way of video circuit 242; a program memory 222 for storing executable computer program code to program the processor 220, and a data memory 223/224 for storing data, such as per-pixel x-ray emission spectra recorded from sample 202 and a library of standardized mineral x-ray emission spectra. Program memory 222 can include computer storage media in the form of removable and/or non-removable, volatile and/or nonvolatile memory and can provide storage of computer-readable instructions, data structures, program modules and other data. Generally, the processor 220 is programmed by means of instructions stored at different times in the various computer-readable storage media. Programs and operating systems are typically distributed, for example, on floppy disks or CD-ROMs. From there, they are installed or loaded into the secondary memory of a computer. At execution, they are loaded at least partially into the computer's primary electronic memory. The invention described herein includes these and other various types of computer-readable storage media when such media contain instructions or programs for implementing the steps described below in conjunction with a microprocessor or other data processor. The invention also includes the computer itself when programmed according to the methods and techniques described herein.

While the embodiment shown uses a scanning electron microscope to generate x-rays from sample 202, other embodiments could employ a transmission electron microscope or a scanning transmission electron microscope. An x-ray fluorescence system could also be used to generate x-rays from sample 202. In other embodiments, different forms of characteristic radiation emitted from the sample, such as gamma rays, may be detected.

Figure 2:
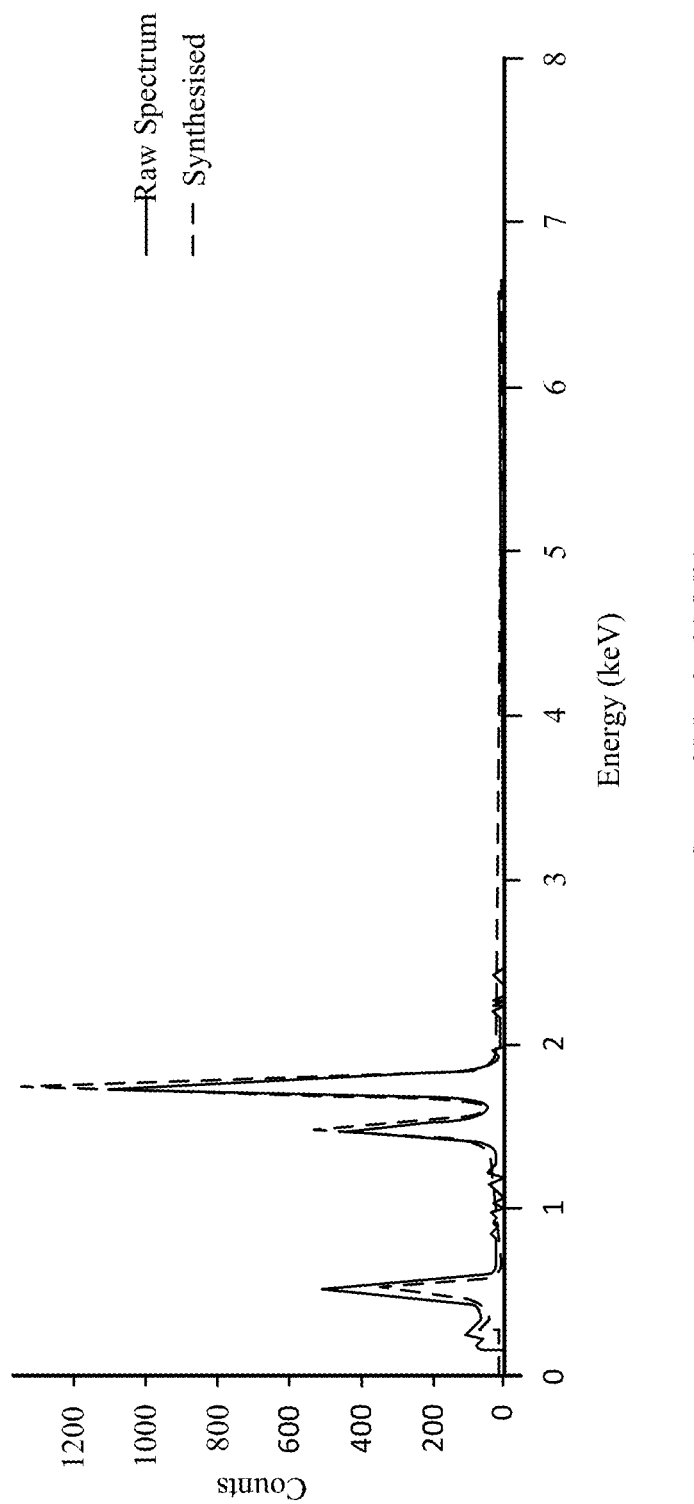
FIG. 2 is an example of a pixel level x-ray emission spectrum obtained from a raster scanned, laboratory generated, Quartz/Kaolinite mineral sample fitted with an x-ray emission spectrum from a mineral combination consisting of 54% Kaolinite and 46% Quartz.

FIG. 2 is an example of a pixel level x-ray emission spectrum obtained from a raster scanned, laboratory generated, Quartz/Kaolinite mineral sample. The measured x-ray spectrum was subsequently fitted to a plurality of standard x-ray mineral spectra using the method described below in reference to FIG. 3 and determined to be a 96% match to an x-ray spectrum from a mixture of 54% Kaolinite and 46% Quartz.

Figure 3:
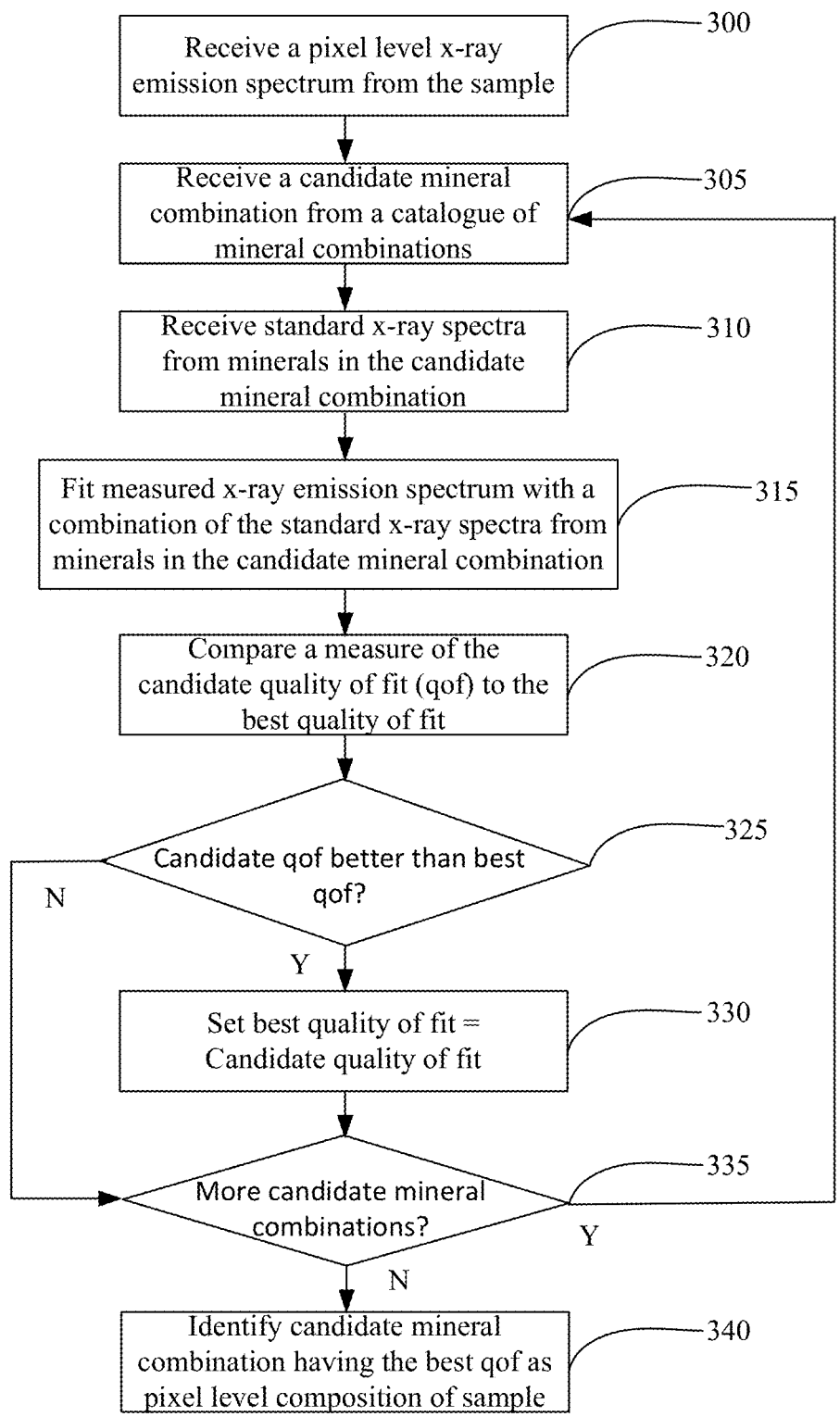
FIG. 3 is a flow chart depicting a general method for identifying the mineral composition of a raster scanned mineral sample containing fine grained minerals.

FIG. 3 is a flow chart depicting a method for identifying the mineral composition of a raster scanned mineral sample containing fine grained minerals. As discussed above, a sample 202 is placed on the sample stage 204 of the mineral identification system 200. The sample is scanned with an electron beam 232 in a raster fashion, and for each pixel of the raster scan, characteristic x-ray emissions are detected by x-ray detector 240 and recorded by processor 220. Processor 220 is programmed to generate a sample x-ray emission spectrum from the detected x-ray emissions, which can be received and stored (300) in the measured spectra memory 222. Also received into memory is a candidate mineral combination from a list of candidate mineral combinations (305). A method for generating the list of candidate mineral combinations is further described below in reference to FIG. 4. In general, a candidate mineral combination can contain as many as m different minerals, and standard x-ray emission spectra for each of the m minerals are also received (310) from a stored library of standard emission spectra 224. Since certain minerals (e.g., Illite) can have a variable elemental composition, more than one x-ray emission spectra can be stored in the library for such minerals. In such cases, all of the stored emission spectra are received whenever the mineral appears in a candidate mineral combination.

Next, the sample x-ray emission spectrum is fit with a linear combination of the standard x-ray emission spectra of the minerals in the candidate mineral combination (315) by determining the proportion $x_j$ of each mineral $m_j$ in the linear combination that makes the best fit. Since the problem is over constrained, an exact fit or solution is not possible, and a least squares or similar minimization algorithm is used to find a solution that minimizes a measure of error between the sample emission spectrum and the linear combination of the standard emission spectra of the minerals in the candidate mineral combination. In one embodiment, the measure of error is the sum over all energy channels of the absolute value of the difference between the sample emission spectrum and the linear combination of the standard emission spectra of the minerals in the candidate mineral combination.

Mathematically, the received sample emission spectrum can be represented as an n×1-dimensional vector $S_s$, whose n rows represent a count of the number of detected x-rays emitted by the sample in each of n energy bins. Similarly, the standard emission spectra for each mineral $m_j$ in the candidate mineral combination can be represented as an n×1-dimensional vector $S_{mj}$, whose n rows represent a count of the number of detected x-rays emitted by a pure sample of the mineral $m_j$ in each of the n energy bins. To account for differences in exposure times, the sample and standard emission spectra can be suitably normalized. For example, the spectra can be normalized to have the same number of counts, or to have to have a given number of counts determined by their respective count rates and a given exposure time.

The proportions $x_j$ of each mineral $m_j$ in the candidate mineral combination can be determined by fitting the received sample emission spectra $S_s$ with the standard emission spectra $S_{mj}$ of the minerals in the candidate mineral combination. This involves finding the solution to the over-constrained linear equation:

$$Ax = S_s \quad \text{(Eq. 1)}$$

where A is an n×m matrix whose m columns are the standard emission spectra $S_{mj}$ of the $m_j$ candidate minerals in the candidate mineral combination, x is an m×1 vector whose entries $x_j$ represent the proportion of each mineral $m_j$ in the candidate mineral combination, and $S_s$ is the n×1 sample x-ray emission spectrum.

In one embodiment, the solution is found by minimizing the least squares error, and in this case, the solution to Eq. 1 is:

$$x = (A^T A)^{-1} A^T S_s \quad \text{(Eq. 2)}$$

where $A^T$ is the m×n transpose of matrix A, $(A^T A)$ is an m×m matrix formed by multiplying the matrices $A^T$ and A, and $(A^T A)^{-1}$ is the m×m inverse of $(A^T A)$. In another embodiment, the solution is found by minimizing the least absolute deviation error, and can be determined using simplex-methods. In this embodiment, the solution can be found using a variety of techniques such as linear programming, iterative gradient descent algorithms including the Levenverg-Marquardt algorithm or the Gauss-Newton algorithm, or using iteratively reweighted least squares.

The x-ray emission spectrum $S_c$ of the candidate mineral combination can then be obtained from the m×1 vector x as:

$$S_c = Ax \quad \text{(Eq. 3)}$$

A measure of the quality of fit (qof) between the x-ray spectrum of the sample and the x-ray spectrum of the candidate mineral combination can then be obtained as:

$$qof = \sum_{1}^{n} |S_c(i) - S_s(i)| \quad \text{(Eq. 4)}$$

where the summation runs over the n energy bins in the sample and candidate mineral combination x-ray spectra. Of course, other measures of the qof are possible. For example, the qof can be the sum of the squares of the per channel differences between the sample x-ray spectrum and the candidate mineral combination x-ray spectrum. Or it can be the root-mean-square of the per channel differences. Other measures are also possible. Moreover, while the qof shown in Eq. 4 gets smaller as the difference between the sample x-ray spectrum and the candidate mineral combination x-ray spectrum gets smaller, a qof can be defined that has the opposite property and gets bigger as the difference between the two spectra gets smaller.

In one embodiment, the qof is determined from a Pearson's $\chi^2$ test, where the value of $\chi^2$ is determined as:

$$\chi^2 = \sum_{i=1}^{n} \frac{(S_c(i) - S_s(i))^2}{S_c(i)} \quad \text{(Eq. 5)}$$

A probability that the candidate mineral combination spectrum $S_c$ matches the sample spectrum $S_s$ is then obtained from a $\chi^2$ distribution for n-m degrees of freedom using the $\chi^2$ value calculated in Eq. 5. This probability, which is bounded between 0 and 1, can be used as a measure of the qof between the sample and candidate spectra. It gets larger as the two spectra are more closely matched, and has the value of 1 when the two spectra are identical.

After the qof between the emission spectra of the sample and the candidate mineral combination is determined, it is compared to a best qof (320). Initially, the best qof can be set to a lowest possible initial value. For example, when the Pearson's $\chi^2$ test is used to determine qof, the best qof can be initialized to zero. When the qof of a current candidate mineral combination is better (e.g., higher) than the best qof, the best qof is set to the qof of the current candidate mineral combination (330).

Next, and regardless of whether the qof of the current candidate mineral combination was better than the best qof, the list of candidate mineral combinations is checked to determine if there are more candidate mineral combinations in the list of candidate mineral combinations (335). If there are, another candidate mineral combination (305) and the standard x-ray spectra for minerals in the candidate mineral combination (310) are received, and the process of fitting the sample x-ray emission spectrum to a linear combination of the x-ray emission spectra of the minerals in the candidate mineral combination (i.e., steps 315 to 335) is repeated.

When no more candidate mineral combinations remain in the list of candidate mineral combinations, the candidate mineral combination associated with the best qof is selected as the mineral combination for that pixel of the sample (340). In some embodiments, the candidate mineral combination associated with the best qof is only selected as the mineral combination for that pixel if it exceeds a minimal value. For example, when the Pearson's $\chi^2$ test is used to determine the quality of fit, the candidate mineral combination associated with the best qof is only selected as the mineral combination for the pixel when it has a qof that exceeds 0.50.

In some embodiments, variations of the fitting algorithm described above can be used. For example, information describing statistical or systematic errors in the emission spectra can be used to weight the individual channels or energies in the emission spectra in the least squares fitting algorithm. Energy channels in the emission spectra that have a high statistical or systematic error can be given a lower weight than energy channels in the emission spectra that have a low statistical or systematic error. In general, each channel of an emission spectrum can be assigned a weight $w_i=1/\sigma_i^2$, where $\sigma_i^2$ is the square of the combined statistical and systematic error for that channel. In such cases the weighted least squares solution for the percentages of each mineral in a candidate mineral combination can be given by:

$$x=(A^TWA)^{-1}A^TWS_s \quad \text{(Eq. 6)}$$

where W is an n×n matrix whose off-diagonal elements are zero, and whose diagonal elements are the weights $w_i=1/\sigma_i^2$ described above.

The mineral combination solution derived from Eq. 6 is particularly useful for fitting a sample spectrum with a candidate mineral combination spectrum in light of systematic counting errors that can occur at both low and high energies. At low energies, x-rays produced in the bulk of the sample are more likely to scatter and not reach the x-ray detector. At high energies, x-ray production falls off as the beam energy approaches the x-ray excitation energy due to beam scattering and energy loss. Both counting errors can be accommodated by appropriately discounting or down-weighting the low and high energy channels in the sample and candidate mineral combination spectra.

For example, minerals that contain oxygen have a low energy peak at around 0.5 keV. But the size of this peak can vary significantly among different spectra of the same mineral due to the tendency of low energy x-rays to scatter prior to reaching the x-ray detector. To account for this, a low weight can be assigned to low energy x-ray counts, thereby allowing the weighted fitting algorithm to correctly fit two spectra even though they may not be a particularly good fit at low energies. In one embodiment, a weight of zero is assigned to the 0.5 keV energy channel corresponding to x-rays produced by minerals containing oxygen, thereby reducing the fitting algorithms sensitivity to lower energy x-rays produced by oxygen containing minerals.

At higher energies, weights can similarly be used to discount the degree to which the high energy peaks in spectra must match in order to consider the spectra as a whole to match. However, the count in high energy peaks is often so low that the peak signal is lost in the noise. To address this issue, the counts in high energy channels are often integrated or sub-sampled over several contiguous energy channels. Moreover, since the problem is a function of energy, more channels are integrated or sub-sampled at higher energies than at lower energies.

In one embodiment, the amount of sub-sampling at any given energy channel is dynamically determined based on the channel's corresponding energy. The sub-sampling adjusts the relative intensity of background radiation in high energy channels to match the intensity of background radiation in a low energy reference energy channel. To determine the number of channels to integrate at a given energy channel, a model of the background x-ray intensity spectrum as a function of energy is generated as shown below in reference to FIG. 8.

Figure 8:
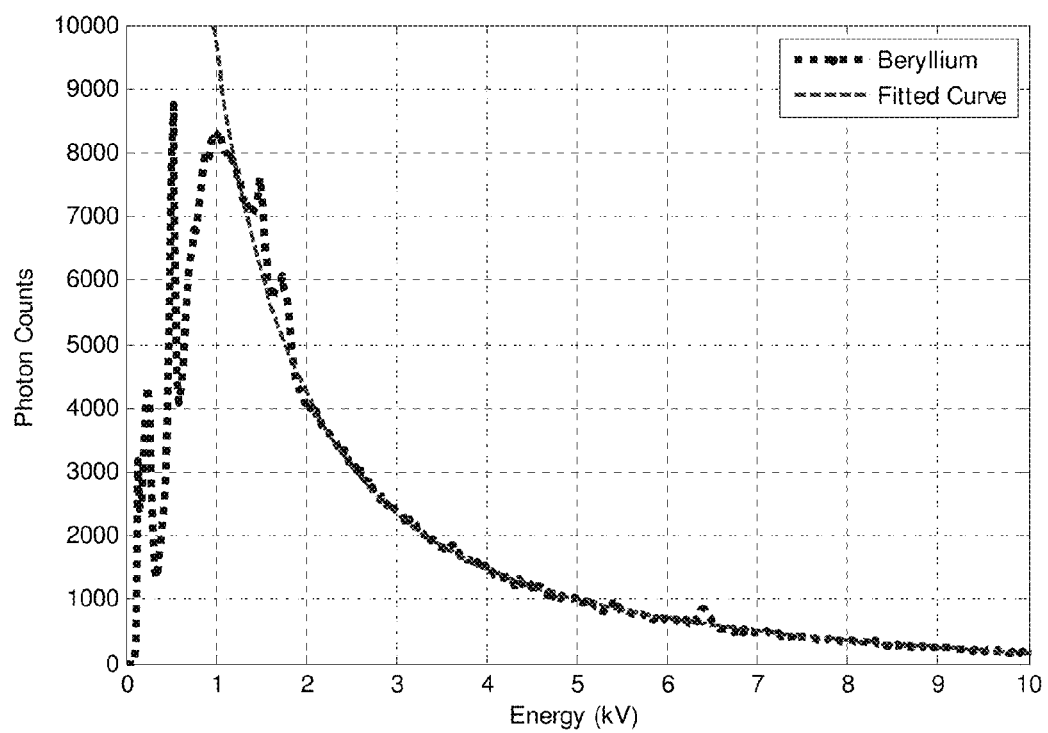
FIG. 8 is an illustration of the x-ray spectrum of Beryllium metal fitted to a curve.

FIG. 8 is an illustration of the x-ray spectrum of Beryllium fitted to a curve. The energy of x-rays emitted by Beryllium are too low to be efficiently detected in an EDS detector, so most of the spectrum depicted in FIG. 8 comes from the Bremsstrahlung radiation emitted by electrons decelerating within the metal. While FIG. 8 depicts the x-ray spectrum of Beryllium, the x-ray spectrum of any low average atomic number element or mineral, such as carbon, quartz etc., can be used for this purpose.

As shown in FIG. 8, a curve has been fitted against the high energy region of the x-ray emission spectrum, from approximately 1.5 kV to 10 kV, to model the effect of fewer x-rays being generated at higher energies. In one embodiment, this curve has the form:

$$y = a_0 e^{-x} + a_1 + \frac{a_2}{x} \quad \text{(Eq. 7)}$$

where x is the energy of a channel, y is the expected intensity of the curve, and $a_0$, $a_1$, and $a_2$ are constants determined by fitting Eq. 7 to the data. In one embodiment, Eq. 7 can be re-written in matrix form as y=Ka, where y is an n×1-dimensional vector whose n rows $y_i$ represent a count of the number of detected x-rays emitted by the Beryllium sample in each of n energy bins, K is an n×3 matrix having n-rows and 3 columns $e^{-x_i}$, 1, and $$\frac{1}{x_i},$$

and a is a 3×1-dimensional vector of constants $a_0$, $a_1$, and $a_2$. This equation is over-constrained for n>3, and is solvable for the constants $a_0$, $a_1$, and $a_2$ using any technique that minimizes an error function between the measured and expected x-ray spectrum intensities. In one embodiment, a least squares solution can be computed directly as $a=(K^TK)^{-1}K^Ty$.

To determine the amount of energy sub-sampling from the background radiation model, a low energy reference point ($x_{REF}$, $y_{REF}$) is first selected. Next, for each energy channel $x_i$, the expected intensity $y_i$ of the background radiation is computed from Eq. 7. The ratio $y_i/y_{REF}$ is then computed and rounded down to the nearest whole number to determine the number of energy channels to integrate or sub-sample at channel $x_i$. Using this procedure, a background radiation spectrum taken from a carbon sample, and a 1 keV reference point, the following table which shows the number of channels sub-sampled as a function of energy was generated.

TABLE 1

| Channel Low Energy Bound (keV) | Channel High Energy Bound (keV) | Number of original channels | Number of sub-sampled channels | Sub-sampling ratio |
| --- | --- | --- | --- | --- |
| 0 | 1.44 | 72 | 72 | 1 |
| 1.44 | 2.16 | 36 | 18 | 2 |
| 2.16 | 2.76 | 30 | 10 | 3 |
| 2.76 | 3.32 | 28 | 7 | 4 |
| 3.82 | 4.18 | 18 | 3 | 6 |
| 4.18 | 4.6 | 21 | 3 | 7 |
| 4.6 | 4.92 | 16 | 2 | 8 |
| 4.92 | 5.28 | 18 | 2 | 9 |
| 5.28 | 5.68 | 20 | 10 | 2 |
| 5.68 | 5.9 | 11 | 1 | 11 |
| 5.9 | 6.14 | 12 | 1 | 12 |
| 6.14 | 6.4 | 13 | 1 | 13 |
| 6.4 | 6.68 | 14 | 1 | 14 |
| 6.68 | 7 | 16 | 1 | 16 |
| 7 | 7.34 | 17 | 1 | 17 |
| 7.34 | 7.72 | 19 | 1 | 19 |
| 7.72 | 8.16 | 22 | 1 | 22 |
| 8.16 | 8.68 | 26 | 1 | 26 |
| 8.86 | 9.32 | 23 | 1 | 23 |
| 9.32 | 10.16 | 42 | 1 | 42 |
| 10.16 | 20.52 | 518 | 7 | 74 |

Figure 9:
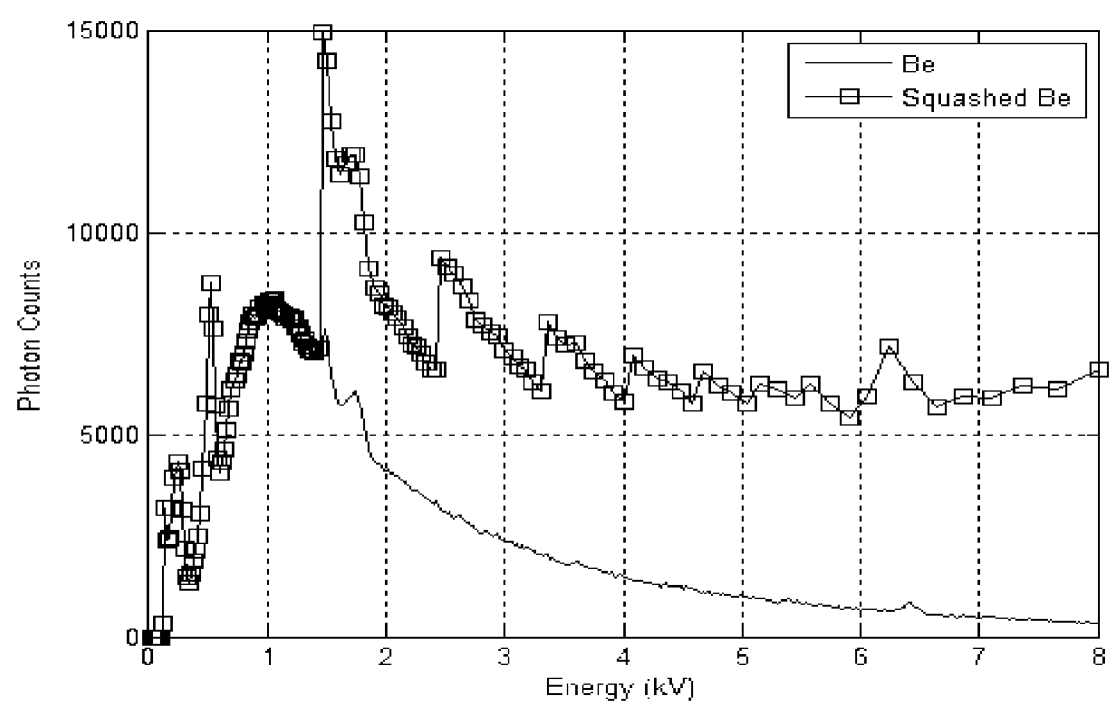
FIG. 9 is an illustration of the x-ray spectrum of Beryllium after being sub-sampled by integrating its high energy channels.

FIG. 9 is an illustration of the x-ray spectrum of Beryllium after being sub-sampled by integrating its high energy channels. The sub-sampled spectrum shows that the background radiation in the sub-sampled channels between 1.5 kV and 10 kV is approximately the same (7000 counts) as the background radiation at 1.5 kV. As a result of the sub-sampling, the small Fe peak at the 6.4 kV sub-sampled energy channel stands out from the background.

Figure 10:
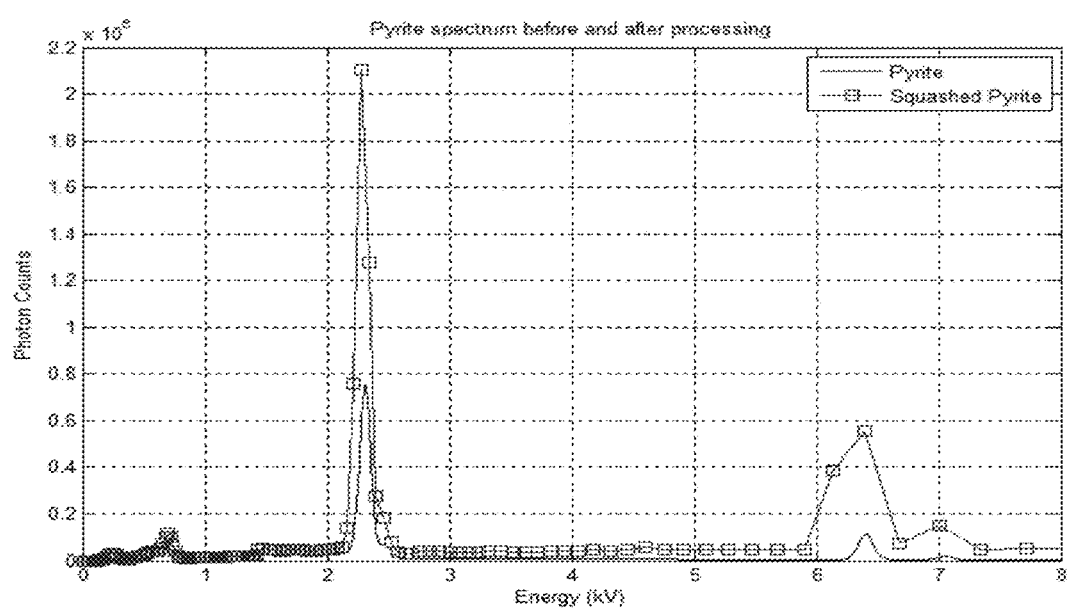
FIG. 10 is an illustration depicting the effect sub-sampling has on x-ray peak heights in a sub-sampled pyrite x-ray emission spectrum.

FIG. 10 is an illustration depicting the effect sub-sampling has on x-ray peak heights in a sub-sampled pyrite x-ray emission spectrum. As shown in the figure, the ratio of the heights of the 6.4 kV Fe peak to the 2.3 kV S peak changes from ~6.5:1 to ~3.8:1 upon sub-sampling the higher energy channels in the pyrite spectrum. The sub-sampling is thus seen to compensate for inherent x-ray detection efficiencies as a function of energy channel, thereby allowing the spectra matching techniques previously disclosed to similarly weigh both higher energy and lower energy x-ray peaks. The Fe peak has a higher relative importance to S in the sub-sampled spectrum, reflecting the system inefficiencies at 6.4 kV relative to 2.3 kV.

Figure 4:
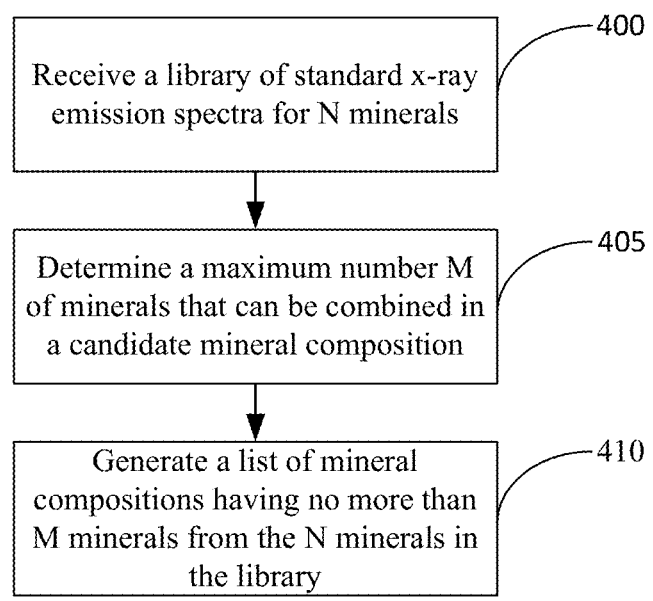
FIG. 4 is a flow chart depicting a method for generating mineral combinations used to identify the mineral composition of a fine grained, raster scanned, mineral sample.

FIG. 4 is a flow chart depicting a method for generating mineral combinations used to identify the mineral composition of a raster scanned, fine grained, mineral sample. The method begins by receiving into memory a library of standard x-ray emission spectra for a number of minerals, N, where N is a whole number (400). In some embodiments, the mineral spectra in the received library can be generated from pure mineral samples using the mineral identification system 200 shown in FIG. 1. The number of minerals in the library can be any whole number, and can be input by a user or set to a default number. The number and type of minerals in the library should in general be large enough to include all minerals that are likely to be found in the scanned mineral sample. Different libraries can be used for different types of samples (e.g., iron ores or aluminum ores) depending on the types of minerals expected to be found in the different types of samples, or a universal library can be used that is valid for testing any and all samples.

For minerals having a variable elemental stoichiometry, more than one mineral spectrum can be included in the library. In some cases, the number of mineral spectra included in the library can be less than the number of stoichiometric variants of the mineral. For example, feldspar is known to have a variable stoichiometry that can be characterized by the relative amounts of Na and K in a sample. As a result, the standard mineral spectra library includes both a Na-rich feldspar spectrum and a K-rich feldspar spectrum. When a sample containing feldspar is analyzed, the described method can not only determine that the sample contains feldspar, but can also determine the particular stoichiometric variant of feldspar in the sample by determining the relative amount of Na-rich and K-rich feldspar in the sample.

Once the number N of mineral spectra stored in the library is determined, a maximum number M of minerals that can be combined in a candidate mineral composition is determined (405). The number M can be any suitable whole number, and can be input by a user or set to a default value. The number M is an upper bound on the number of minerals whose x-ray emission spectra can be combined when fitting the scanned sample x-ray emission spectrum. In general, increasing M increases the extent to which the x-ray emission spectra of the best mineral combination fits the x-ray emission spectrum of the scanned sample, but also geometrically increases the time required to perform the mineral identification analysis since more candidate mineral combination spectra must be fit to the sample spectrum in order to identify the best fitting mineral combination. In one embodiment, M is set to a default value of 3 in order to reasonably identify the minerals in the scanned sample in a reasonable amount of time.

Finally, a list of mineral compositions having no more than M minerals per composition is generated from the N minerals in the standard mineral library. The list of mineral compositions can be generated by first adding all N minerals from the library to the list. Next, all combinations of any two minerals from the library are added to the list. Next, all combinations of any 3, 4, 5 . . . , M−1, M minerals from the library are added to complete the list. For example, if the mineral library consists of 5 minerals where no more than 3 can be combined to form a mineral composition, the list of mineral compositions would be generated by adding to an empty set the 5 minerals in the library, the 10 possible combinations of any two minerals in the library, and the 10 possible combinations of any three minerals in the library. The completed list can then be used to provide the candidate mineral compositions whose standard x-ray mineral spectra are combined and fitted to the sample mineral spectrum as described above in reference to FIG. 3. Note that when one of the minerals in a candidate mineral composition is associated with more than one standard mineral spectrum in the library (e.g., feldspar having both a Na-rich spectrum and a K-rich spectrum), all of the associated spectra for that mineral are combined and fitted to the sample mineral spectrum when the mineral is present in a candidate mineral combination.

Figure 5:
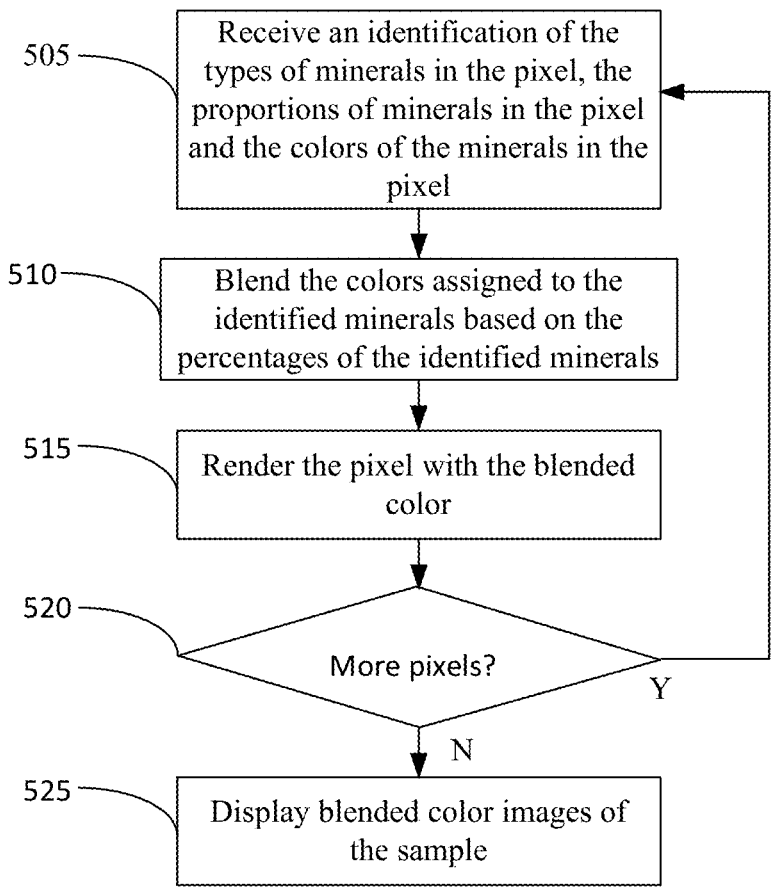
FIG. 5 is a flow chart illustrating a method for displaying the identified mineral composition of a raster scanned, fine grained, mineral sample on a per pixel basis.

FIG. 5 is a flow chart illustrating a method for displaying an image identifying on a per pixel basis the mineral composition of a raster scanned, fine grained, mineral sample. The mineral sample can be raster scanned, for example, using the system shown in FIG. 1, and the per pixel composition of the raster scanned mineral sample can be determined using the method shown in FIG. 3. An image displaying the mineral composition of the sample can be created by receiving, on a per pixel basis, the identity of the minerals assigned to the pixel, the relative proportion of the identified minerals, and a color that has been assigned to each of the identified minerals (505). As noted above, the data memory 223/224 shown in FIG. 1 is configured to store a library of standard mineral x-ray emission spectra. The data memory 223/224 can also be configured to associate and store a unique color for each mineral in the library. Thus, for example, quartz can be associated with blue, Kaolinite with red, Elite with green, and muscovite with yellow.

Once the minerals, their proportions, and their associated colors have been received, the colors of the identified minerals can be blended based on their proportion. Any color blending technique can be used. For example, the Adobe Photoshop application allows pixels to be composited from multiple layers, where each layer consists of a color channel and an alpha channel. When a pixel is rendered, its color is determined by compositing the color of each layer according to its alpha channel, thereby blending or mixing the color of each layer in proportion to its alpha channel. Of course, other techniques that blend the colors assigned to the identified minerals based on their proportions can be used. Once blended, the image pixel is rendered with the blended color (515). If more pixels of the raster scanned mineral sample remain (520), they can be similarly rendered according to the process described (505-520). When all pixels have been rendered, an image of the sample whose pixels have blended colors that reflect the identified mineral content in those pixels can be displayed (525). For those pixels for which the mineral identification process described in FIG. 3 has failed (e.g., for those having a best matching probability of less than 50%) a default color such as white or black can be assigned to the pixel.

Figure 6:
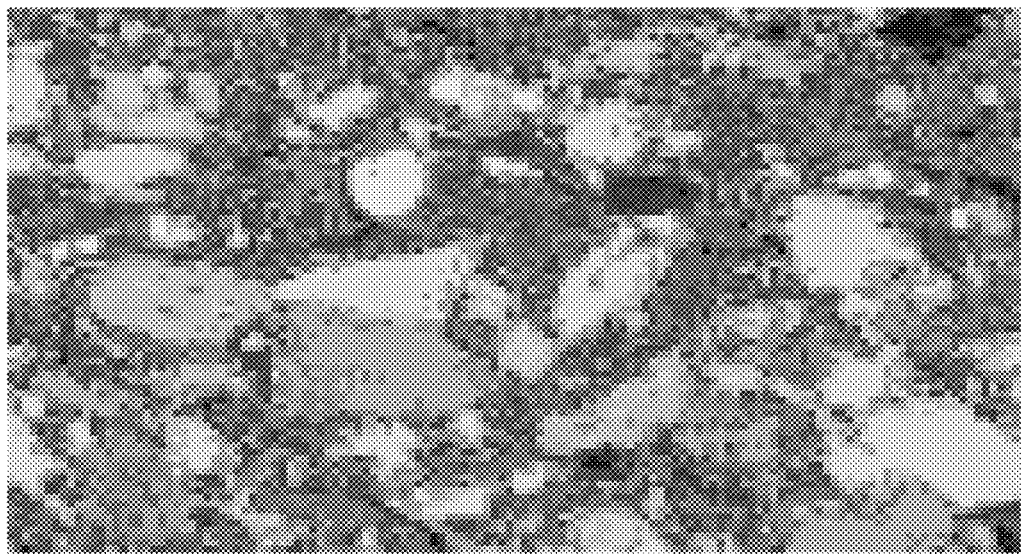
FIG. 6 is an illustration of a display of the identified mineral composition of a raster scanned, fine grained, mineral sample made according to the method of FIG. 5.

FIG. 6 is an illustration of a display of an image showing the identified mineral composition of a raster scanned, fine grained, mineral sample generated using the mineral identification and display methods and apparatus illustrated in FIGS. 1, 3 and 5. As shown in FIG. 6, different pixels of the image have different colors representing the different minerals or combinations of minerals identified in those pixels. Large mineral grains appear in uniformly colored regions, and boundaries between large mineral grains appear as blended colors reflecting the presence of multiple minerals in different proportions in the pixels along the grain boundaries. The matrix of fine grained minerals within which the large mineral grains are suspended appears as a continuously varying hue of a dominant color (e.g., green), reflecting the presence of multiple minerals in varying proportions in different areas of the matrix.

Figure 7:
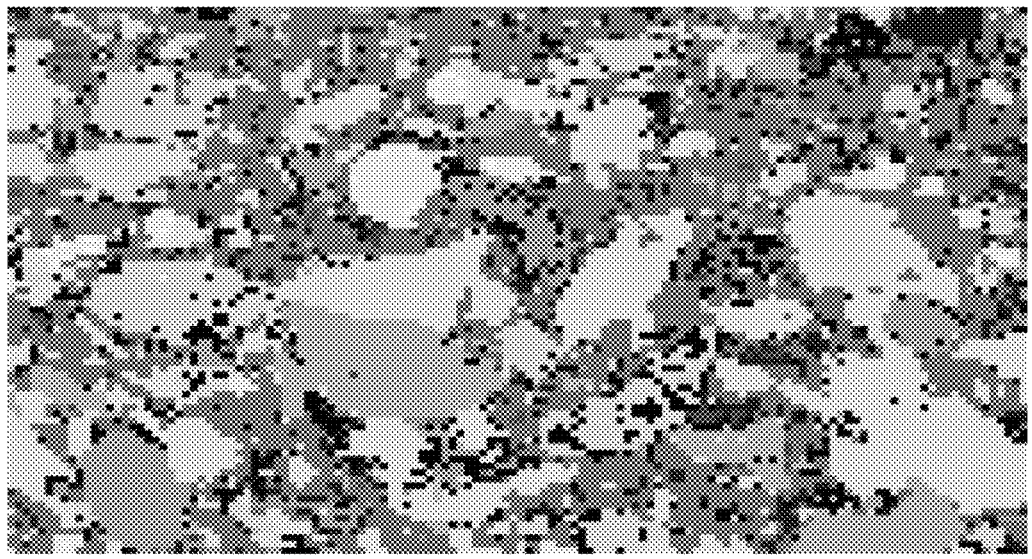
FIG. 7 is an illustration of a display of the identified mineral composition of a raster scanned, fine grained, mineral sample made using a prior art method that assigned a single mineral to each pixel in the sample.

The superior quality of the image shown in FIG. 6 can be seen by comparing it to an image of the same mineral sample analyzed using conventional mineral identification techniques in which each pixel is assigned a single mineral and color. Such an image is shown in FIG. 7. Compared to the smooth and blended image shown in FIG. 6, the prior art image shown in FIG. 7 appears rigid and disjoint. While the large grained minerals appear to have roughly the same size and shape and appear in the same position in FIGS. 6 and 7, some differences can be seen. More clearly visible is the difference in the display of the boundaries between the large grained minerals or the boundaries between the large grained minerals and the matrix. The image displayed in FIG. 6 clearly shows a richness and complexity in these areas that is completely absent from FIG. 7. Moreover, while FIG. 7 shows the matrix to have a nearly uniform color and therefore a near uniform composition, FIG. 6 shows the matrix to have highly variable blended colors and therefore a very rich and complex mineral composition. In addition to providing superior information on the nature and complexity of the sample matrix, the image shown in FIG. 6 also provides finer details of the large grain minerals in the sample. This allows for better grain size calculations, which are important in certain applications such as oil and gas reservoir characterization.

Although the present invention and its advantages have been described in detail, it should be understood that various changes, substitutions and alterations can be made to the embodiments described herein without departing from the spirit and scope of the invention as defined by the appended claims. Moreover, the scope of the present application is not intended to be limited to the particular embodiments of the process, machine, manufacture, composition of matter, means, methods and steps described in the specification. As one of ordinary skill in the art will readily appreciate from the disclosure of the present invention, processes, machines, manufacture, compositions of matter, means, methods, or steps, presently existing or later to be developed that perform substantially the same function or achieve substantially the same result as the corresponding embodiments described herein may be utilized according to the present invention. Accordingly, the appended claims are intended to include within their scope such processes, machines, manufacture, compositions of matter, means, methods, or steps.

We claim as follows:

1. A computer implemented method for displaying a mineral composition of a sample, comprising:
    illuminating a portion of the sample with a charged particle beam;
    generating, via one or more processors, a sample emission spectrum from detected emissions from the sample;
    fitting the sample emission spectrum with a plurality of candidate emission spectra, wherein each candidate emission spectrum comprises a combination of the emission spectra from a plurality of minerals in proportions that are determined by the fit to the sample emission spectrum;
    identifying an emission spectrum from among the plurality of candidate emission spectra based on a quality of fit to the sample emission spectrum, wherein the identified emission spectrum comprises a plurality of identified minerals in a respective plurality of identified proportions;
    assigning a plurality of colors respectively corresponding to the plurality of identified minerals; and
    rendering an image pixel corresponding to the illuminated portion of the sample by assigning the image pixel a definite color based on the plurality of identified minerals by blending the plurality of colors respectively corresponding to the plurality of identified minerals according to the respective plurality of identified proportions.

2. The method of claim 1, wherein the charged particle beam is at least one of an electron beam, a proton beam or an ion beam.

3. The method of claim 1, wherein generating the sample emission spectrum from detected emissions from the sample comprises generating a sample x-ray emission spectrum from detected x-ray emissions from the sample.

4. The method of claim 1, wherein fitting the sample emission spectrum with a plurality of candidate emission spectra comprises using a curve fitting minimization technique to fit the sample emission spectrum with the plurality of candidate emission spectra.

5. The method of claim 1, wherein generating the sample emission spectrum from detected emissions from the sample further comprises sub-sampling the emission spectrum as a function of energy.

6. The method of claim 1, wherein fitting the sample emission spectrum with a plurality of candidate emission spectra further comprises using a weighted curve fitting minimization technique to fit the sample emission spectrum with the plurality of candidate emission spectra.

7. A computer implemented method for displaying a mineral composition of a sample, comprising:
 illuminating a portion of the sample with a charged particle beam;
 generating, via one or more processors, a sample emission spectrum from detected emissions from the sample;
 receiving a plurality of candidate mineral compositions from a list of candidate mineral compositions, wherein each candidate mineral composition includes a plurality of minerals;
 determining, for each of the plurality of candidate mineral compositions, a proportion for each of the plurality of minerals in the candidate mineral composition by fitting the sample emission spectrum with a candidate emission spectrum formed from a combination of emission spectra from the plurality of minerals in the candidate mineral composition;
 identifying a candidate mineral composition whose candidate emission spectrum is a best fit to the sample emission spectrum;
 assigning a plurality of colors respectively corresponding to the plurality of minerals in the identified candidate mineral composition; and
 rendering an image pixel corresponding to the illuminated portion of the sample by assigning the image pixel a definite color based on the plurality of identified minerals through blending the plurality of colors respectively corresponding to the plurality of minerals in the identified candidate mineral composition according to the determined proportion for each of the plurality of minerals.

8. The method of claim 7, wherein the charged particle beam is at least one of an electron beam, a proton beam or an ion beam.

9. The method of claim 7, wherein generating the sample emission spectrum from detected emissions from the sample comprises generating a sample x-ray emission spectrum from detected x-ray emissions from the sample.

10. The method of claim 7, wherein generating the sample emission spectrum from detected emissions from the sample further comprises sub-sampling the sample emission spectrum as a function of energy.

11. The method of claim 7, wherein fitting the sample emission spectrum with a plurality of candidate emission spectra further comprising using a weighted least squares algorithm to fit the sample emission spectrum with the plurality of candidate emission spectra.

12. An apparatus for determining and displaying a mineral composition of a sample, comprising:
 a charged particle beam source for illuminating a portion of the sample;
 a detector for detecting radiation emitted from the illuminated portion of the sample; and
 one or more processors configured to:
  generate a sample emission spectrum from the detected radiation emitted from the illuminated portion of the sample;
  fit the sample emission spectrum with a plurality of candidate emission spectra, wherein each candidate emission spectrum comprises a combination of the emission spectra from a plurality of minerals in proportions that are determined by the fit to the sample emission spectrum;
  identify an emission spectrum from among the plurality of candidate emission spectra based on a quality of fit to the sample emission spectrum, wherein the identified emission spectrum comprises a plurality of identified minerals in a respective plurality of identified proportions;
  assign a plurality of colors respectively corresponding to the plurality of identified minerals; and
  render an image pixel corresponding to the illuminated portion of the sample by assigning the image pixel a definite color based on the plurality of identified minerals by blending the plurality of colors respectively corresponding to the plurality of identified minerals according to the respective plurality of identified proportions.

13. The apparatus of claim 12, wherein the charged particle beam source is at least one of an electron beam source, a proton beam source or an ion beam source.

14. The apparatus of claim 12, wherein the one or more processors generate the sample emission spectrum from the detected radiation emitted from the illuminated portion of the sample by generating a sample x-ray emission spectrum from detected x-ray emissions from the sample.

15. The apparatus of claim 12, the one or more processors fit the sample emission spectrum with a plurality of candidate emission spectra using a least squares analysis.

16. An apparatus for determining and displaying a mineral composition of a sample, comprising:
 a charged particle beam source for illuminating a portion of the sample;
 a detector for detecting radiation emitted from the illuminated portion of the sample; and
 one or more processors configured to:
  generate a sample emission spectrum from the detected radiation emitted from the illuminated portion of the sample;
  receive a plurality of candidate mineral compositions from a list of candidate mineral compositions, wherein each candidate mineral composition includes a plurality of minerals;
  determine, for each of the plurality of candidate mineral compositions, a proportion for each of the plurality of minerals in the candidate mineral composition by fitting the sample emission spectrum with a candidate emission spectrum formed from a combination of emission spectra from the plurality of minerals in the candidate mineral composition;
  identify a candidate mineral composition whose candidate emission spectrum is a best fit to the sample emission spectrum;
  assign a plurality of colors respectively corresponding to the plurality of minerals in the identified candidate mineral composition; and
  render an image pixel corresponding to the illuminated portion of the sample by assigning the image pixel a definite color based on the plurality of identified minerals by blending the plurality of colors respectively corresponding to the plurality of minerals in the identified candidate mineral composition according to the determined proportion for each of the plurality of minerals.

17. The apparatus of claim 16, wherein the charged particle beam source is at least one of an electron beam source, a proton beam source or an ion beam source.

18. The apparatus of claim 16, wherein the one or more processors generate the sample emission spectrum from the detected radiation emitted from the illuminated portion of the sample by generating a sample x-ray emission spectrum from detected x-ray emissions from the sample.

* * * * *